United States Patent
Lo et al.

(10) Patent No.: US 9,326,938 B2
(45) Date of Patent: May 3, 2016

(54) OLIGOMER-CONTAINED NANOPARTICLE COMPLEX RELEASE SYSTEM

(71) Applicant: National Yang Ming Unviversity, Taipei (TW)

(72) Inventors: Chun-Liang Lo, Taipei (TW); Yi-Ting Chiang, Kaohsiung (TW); Yung-Ting Cheng, Taipei (TW); Chi-Yang Lu, Sansing Township, Yilan County (TW)

(73) Assignee: NATIONAL YANG MING UNIVERSITY, Taipei (TW)

( * ) Notice: Subject to any disclaimer, the term of this patent is extended or adjusted under 35 U.S.C. 154(b) by 196 days.

(21) Appl. No.: 14/100,425

(22) Filed: Dec. 9, 2013

(65) Prior Publication Data

US 2014/0363490 A1 Dec. 11, 2014

(30) Foreign Application Priority Data

Jun. 11, 2013 (TW) .............................. 102120666 A

(51) Int. Cl.
*A61K 9/14* (2006.01)
*A61K 9/127* (2006.01)
*A61K 31/704* (2006.01)
*A61K 9/00* (2006.01)
*A61K 47/48* (2006.01)

(52) U.S. Cl.
CPC .............. *A61K 9/127* (2013.01); *A61K 9/0019* (2013.01); *A61K 31/704* (2013.01); *A61K 47/48815* (2013.01); *Y10S 977/773* (2013.01); *Y10S 977/906* (2013.01); *Y10S 977/907* (2013.01); *Y10S 977/911* (2013.01)

(58) Field of Classification Search
None
See application file for complete search history.

(56) References Cited

U.S. PATENT DOCUMENTS

| 5,543,158 | A | * | 8/1996 | Gref | ..................... | A61K 9/0019 424/451 |
| 2008/0241892 | A1 | * | 10/2008 | Roitman | ................ | C12N 11/14 435/91.2 |
| 2008/0317840 | A1 | * | 12/2008 | Lee | ..................... | A61K 9/1271 514/1.1 |

OTHER PUBLICATIONS

RS Burke, SH Pan. "Synthesis and Characterization of Biodegradable HPMA-Oligolysine Copolymers for Improved Gene Delivery." Bioconjugate Chemistry, vol. 21, 2010, pp. 140-150.*
E Carrlee. "What Do We Know About PEG?" https://ellencarrlee.wordpress.com/2009/04/08/what-do-we-know-about-peg/, published Apr. 8, 2009, accessed Aug. 20, 2015, 17 printed pages.*

(Continued)

*Primary Examiner* — Isaac Shomer
(74) *Attorney, Agent, or Firm* — Muncy, Geissler, Olds & Lowe, P.C.

(57) ABSTRACT

An oligomer-contained nanoparticle complex is provided. The oligomer-contained nanoparticle complex of the invention comprises (a) a nanoparticle, (b) a polymer with high molecule weigh, (c) a target molecule, (d) an oligomer, wherein the oligomer is crosslinked with the polymer by the intermolecular hydrogen bonds or electron bonds, and e) a space for active substances, wherein the space for active substances is encapsulated by the nanoparticle. The oligomer-contained nanoparticle complex of the invention has the high stability and fast drug release rate, and would not be largely accumulated in normal tissues. The invention also provides a method for preparing the oligomer-contained nanoparticle complex and the method for releasing drug.

23 Claims, 20 Drawing Sheets
(3 of 20 Drawing Sheet(s) Filed in Color)

(56) References Cited

OTHER PUBLICATIONS

JM Benns, A Maheshwari, DY Furgeson, RI Mahato, SW Kim. "Folate-PEG-Folate-Graft-Polyethylenimine-Based Gene Delivery." Journal of Drug Targeting, vol. 9 No. 2, 2001, pp. 123-139.*

Y-T Chiang, Y-T Cheng, C-Y Lu, Y-W Yen, L-Y Yu, K-S Yu, S-Y Lyu, C-Y Yang, C-L Lo. "Polymer-Liposome Complexes with a Functional Hydrogen-Bond Cross-Linker for Preventing Protein Adsorption and Improving Tumor Accumulation." Chemistry of Materials, vol. 25, 2013, pp. 4364-4372, published Oct. 14, 2013.*

Chiang, Yi-Ting et al., Polymer-Liposome Complexes with a Functional Hydrogen-Bond Cross-Linker for Preventing Protein Adsorption and Improving Tumor Accumulation, American Chemical Society: Chemistry of Matericals, 2013, pp. 4364-4372.

* cited by examiner

OLIGOMER-CONTAINED NANOPARTICLE COMPLEX RELEASE SYSTEM

CROSS-REFERENCE TO RELATED APPLICATIONS

This Non-provisional application claims priority under 35 U.S.C. §119(a) on Patent Application No(s). 102120666 filed in Taiwan, Republic of China, Jun. 11, 2013, the entire contents of which are hereby incorporated by reference.

FIELD OF THE INVENTION

The present invention relates to an oligomer-contained nanoparticle complex, and in particular relates to an oligomer-contained nanoparticle complex release system with high stability, and high release rate.

BACKGROUND OF THE INVENTION

Nanoparticle technology has been developed for decades. Since nanoparticles have low toxicity and biocompatibility, nanoparticles are widely used in pharmaceutical formulations. The highly toxic drugs may be carried and encapsulated into the inside of nanoparticles to decrease their toxicity. However, nanoparticles have some main defects: low stability in blood, slow drug release, and large normal tissues accumulation. To overcome the defects, physical or chemical technology have been used for the past few years to improve nanoparticle. The combination of high molecular materials and nanoparticles can improve the defects, significantly. However, the disadvantages of low stability in blood and normal tissues accumulation still cannot be overcame, and they also influence the application of the nanoparticle release system in the field of biomedicine.

Nanoparticles are self-assembled vesicles having a spherical bilayer structure surrounding an aqueous core domain. Due to their intrinsic biocompatibility and ease of preparation, several nanoparticle drug systems have been approved. In addition, modified nanoparticles have been shown to have excellent pharmacokinetics profiles for the delivery of nucleic acids, proteins, and chemotherapeutic agents such as doxorubicin. However, major drawbacks of nanoparticle-based drug carriers include their instability and the lack of tunable triggers for drug release. As such, there have been several attempts at enhancing the properties of nanoparticles. For example, incorporation of polymerizable lipid amphiphiles leads to crosslinked nanoparticles with higher stability. Unfortunately, every nanoparticle would require a specific polymerizable amphiphile, making this approach synthetically cumbersome.

In addition, the crosslinks and modification of high molecule often allow for controllable release of the payload. To provide a combination of stability and modification generality, hydrophilic polymers such as poly(ethylene glycol) (PEG) have been added to liposomes. However, these modifiers can easily dissociate from the liposome surface, returning them to the unstable state. In addition, nanoparticle formed by covalent linkage of polymer still have the disadvantages of protein absorption, low drug release and large accumulation in normal tissues. Thus, there are a lot of adverse effects resulting from the use of nanoparticle. For example, (1) the active substance cannot be delivered to and released in the target site since nanoparticle is absorbed with protein resulting in the unstable of nanoparticle; (2) the active substance is largely accumulated in normal tissues that result in metabolism problems.

Accordingly, a novel nanoparticle is required to avoid protein absorption, low drug release rate, and the large accumulation in normal tissues. The nanoparticle with high stability and high release rate can deliver the drug to target cell and avoid protein absorption. Therefore, the amount of drug and side-effect caused by drugs can be decreased to reduce the risk of death attributed to the side-effect of medicine.

BRIEF SUMMARY OF INVENTION

In view of the fact set forth above, the invention provides an oligomer-contained nanoparticle complex and an active substance release system, wherein the "oligomer" has a molecule weight of 200-1,000. The complex is composed of nanoparticle, polymer, and oligomer. The oligomer is crosslinked by hydrogen bonds or electronic bonds so that the nanoparticle complex has the advantages of a high stability, high release rate, low protein absorption, and it can be accumulated in normal tissue(s) or organ(s).

The invention provides an oligomer-contained nanoparticle complex, comprising a) a nanoparticle, b) a polymer, c) an oligomer, d) a targeting molecule, wherein the oligomer is crosslinked with the polymer, and that can reduce the protein absorption and increase the stability of nanoparticle structure, and e) a space for storage active substance.

In one embodiment of the invention, the oligomer and polymer is crosslinked by intermolecular hydrogen bond or electron bond.

In one embodiment of the invention, the oligomer comprises poly(ethylene glycol) (PEG).

In one embodiment of the invention, the polymer comprises a hydrophilic group and a hydrophobic group, wherein the hydrophilic group is selected from amino acid (such as, histidine), N-(2-hydroxypropyl)methacrylamide (HPMA), and high-molecule weight PEG; and the hydrophobic group is selected from cholesterol.

In one embodiment of the invention, the both ends of oligomer are conjugated with a targeting molecule, individually, and the targeting molecule and the polymer are crosslinked by intermolecular hydrogen bond(s) or electron bond(s).

In one embodiment of the invention, the targeting molecule comprises biotin.

In one embodiment of the invention, further comprising an active substance located in the nanoparticle.

In one embodiment of the invention, the active substance includes, but is not limited to, hormone, drug, toxin, cytotoxic agent, pharmaceutically active protein, immunoglobulin, DNA, or RNA.

The invention further provides an active substance release system, comprising the oligomer-contained nanoparticle complex of the invention and an active substance, wherein the active substance is encapsulated in the oligomer-contained nanoparticle complex.

The invention further provides a method for delivering an oligomer-contained nanoparticle complex, comprising administrating the oligomer-contained nanoparticle complex to a subject, and the active substance is released from the oligomer-contained nanoparticle complex at a particular pH condition.

In one embodiment of the invention, the particular pH condition is pH 4 to 6.8.

A detailed description is given in the following embodiments with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention can be more fully understood by reading the subsequent detailed description and examples with references made to the accompanying drawings, wherein:

FIG. 7a-1 shows the distribution of Dox-loaded nanoparticle complex without oligomer in mice at 6 hours after injection;

FIG. 7a-2 shows the distribution of Dox-loaded oligomer-contained nanoparticle complex in mice at 6 hours after injection;

FIG. 7a-3 shows the distribution of Dox-loaded nanoparticle complex without oligomer in mice at 24 hours after injection;

FIG. 7a-4 shows the distribution of Dox-loaded oligomer-contained nanoparticle complex in mice at 24 hours after injection;

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides an oligomer-contained nanoparticle complex, comprising a) a nanoparticle, b) a polymer, c) an oligomer, and d) a targeting molecule, wherein the oligomer is crosslinked with the polymer by hydrogen bond, and e) a space for storage active substance The term "oligomer" of the invention refers to a molecular weight of 200-1,000 Dalton.

The term "nanoparticle" of the invention refers to any lipid structure formed by phospholipid. The phospholipids include, but are not limited to, phosphatidylcholine, disteaorylphosphatidylcholine (DSPC), dimyristoylphosphatidylcholine (DMPC), dipalmitoylphosphatidylcholine (DPPC), and dipalmitoylphosphatidylethanolamine (DPPE). The diameter of the nanoparticle ranges between 0.05 µm and 5 µm, preferably between 0.02 µm and 0.12 µm.

Figure 1:
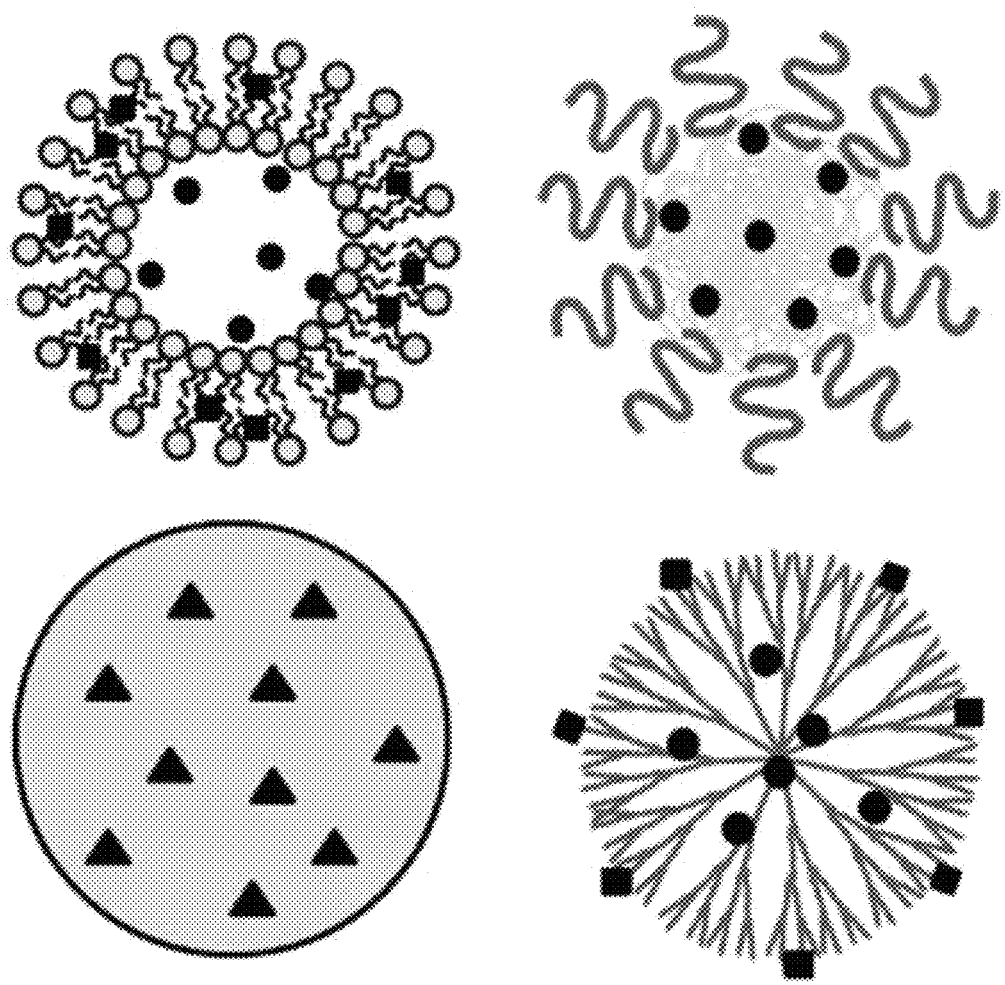
FIG. 1 is a schematic diagram showing the nanoparticle of the invention.

The nanoparticle may be a polymeric micelle and a solid lipid nanoparticle individually and simultaneously. The polymeric micelle is formed by self-assembly of amphiphilic copolymers via hydrophobic and hydrophilic interaction, hydrogen bond, Van der Waals forces, and electrostatic. With respect to the solid lipid nanoparticle, a natural or synthetic solid lipid or fatty acid, or wax is used as a matrix, and inside of the nanoparticle have a capacity space which is located in the phospholipids (sphere), or inserted in membranes, or between the membranes (FIG. 1) to form solid lipid nanoparticles with a diameter of 50-1,000 nm, preferably, 0.05 µm-5 µm.

It shall be noted that the nanoparticle includes at least one hydrophilic or charged oligomer. The hydrophilic or charged oligomer includes, but is not limited to, polyethyleneglycol (PEG), polyvinylpyrrolidone (PVP), polyvinylmethylether (PVME), polymethyloxazoline (PMOX), polyethyloxazoline (PEOX), polyhydroxypropyloxazoline, polyhydroxypropylmethacrylamide (PHPMA), polymethacrylamide (PMA), polydimethylacrylamide (PDMA), polyhydroxypropylmethacrylate, polyhydroxyethylacrylate (PHEA), hydroxymethylcellulose (HMC), hydroxyethylcellulose (HEC), and polyamino acids, preferably, PEG. Generally, the molecule weight of PEG is between 200 and 2,000 Mw, preferably, between 200 and 1,000 Mw.

In one embodiment, the hydrophilic or charged oligomer may be bonded with at least one targeting molecule. The term "targeting molecule" of the invention includes, but is not limited to, folic acid, peptides, proteins, enzymes, lectins, biotin, avidin, mono-, oligo-, and polysaccharides, hormones, cytokines, polyclonal and monoclonal antibodies including chimeric and humanized ones and their fragments. It shall be noted that the hydrophilic or charged oligomer and targeting molecule are conjugated by covalent bonds.

The hydrophilic group of the amphiphilic high molecular polymer includes, but is not limited to, polyhydroxypropylmethacrylamide (PHPMA), polyvinylpyrrolidone (PVP), polyvinylmethylether (PVME), polymethyloxazoline (PMOX), polyethyloxazoline (PEOX), polyhydroxypropyloxazoline, polyhydroxypropylmethacrylamide (PHPMA), polymethacrylamide (PMA), polydimethylacrylamide (PDMA), polyhydroxypropylmethacrylate, polyhydroxyethylacrylate (PHEA), hydroxymethylcellulose (HMC), hydroxyethylcellulose (HEC), polyamino acids, chondroitin sulfate, soluble polyurethane formed by PEG and lysine via covalent bonds, poly(hydroxypropylglutamine), and PET-dendrimer, etc. The hydrophobic group of the amphiphilic high molecular polymer includes, but is not limited to, cholesterol, lipids, hydrophobic polymers, such as poly lactic acid (PLA). It shall be noted that the polymer of the invention shall contain a hydrophilic or charged amino acids, such as histidine, lysine, and arginine, etc. The amphiphilic high molecular polymer and oligomer-targeting molecule are crosslinked by intermolecular hydrogen bonds or electron bonds, and not covalent bonds.

In the invention, the hydrophilic or charged polymer is bonded with oligomer-targeting molecule to cover the surface of the phospholipid of the oligomer-contained nanoparticle complex. That can avoid the phospholipids contacting outside proteins so that the active substance would not be exposed to the oligomer-contained nanoparticle complex. When the oligomer-contained nanoparticle complex enters extracellular matrix, the oligomer-contained nanoparticle complex would be internalized into target cells (cancer cells) by targeting molecules. In one embodiment, the ratio by weight of the oligomer, nanoparticle, and polymer is in a range between 0.5:2:1 and 2:2:1.

In one embodiment, the amphiphilic high molecule polymer is preferably composed of histidine (His), cholesterol (Chol), polyethyleneglycol (PEG), and/or N-(2-hydroxypropyl)methacrylamide (HPMA), etc. The amphiphilic high molecule polymer may be a P(His-Chol), P(HPMA-co-His)-Chol, PEG-PHis-Chol, PEG-HPMA-PHis-Chol, or PEG-P(HPMA-co-His)-Chol. One skilled in art would change the ratio and combination between His, Chol, PEG, and HPMA depending on the different needs.

The invention further provides a method for manufacturing an oligomer-contained nanoparticle complex, comprising a) providing a nanoparticle, b) mixing the nanoparticle and a polymer to form a polymer-incorporated nanoparticle, c) mixing the polymer-incorporated nanoparticle and a oligomer to form a oligomer-contained nanoparticle complex. The detail manufacture processes are shown in Example 1 of the specification.

The invention further provides an active substance release system, comprising the oligomer-contained nanoparticle complex of the invention and an active substance, wherein the active substance is encapsulated by the oligomer-contained nanoparticle complex.

The active substance to be delivered is preferably a hormone, drug, prodrug, toxin, cytotoxin, pharmaceutically active protein, immunogen, DNA, or RNA. Cytotoxic agents, according to the invention, include, but are not limited to alkylating agents, anthracycline antitumor antibiotics, antimetabolites, and metallopeptides containing platinum, copper, vanadium, iron, cobalt, gold, cadmium, zinc and nickel. The active substance can be delivered into the cell by the nanoparticles.

The invention further provides a method for delivering an oligomer-contained nanoparticle complex. The method of the invention comprises:

providing an oligomer-contained nanoparticle complex in a condition, wherein the oligomer-contained nanoparticle complex comprises a oligomer, a polymer, an nanoparticle, and an active substance;

depositing the complex at a neutral condition (pH 7 to pH 8), wherein the complex is stable in the neutral condition;

adjusting the neutral condition to a weak acidic condition (pH 6 to pH 6.8), wherein the targeting molecules of the complex is dissociated at the weak acidic condition; and adjusting the weak acidic condition to a acidic condition (pH 4 to pH 6), wherein the active substance of the complex is released at the acidic condition.

The term "cell" or "target cell" of the invention refers to a cell obtained from human or non-human mammal, e.g. a dog, a cat, a mouse, a rat, a cow, a sheep, a pig, a goat, or a primate, and expressly includes laboratory mammals, livestock, and domestic mammals. In one embodiment, the mammal may be a human; in others, the mammal may be a rodent, such as a mouse or a rat. In another embodiment, the subject is an animal model (e.g., a transgenic mouse model). Alternatively, the subject is a patient preferably, cancer patient.

Figure 2A:
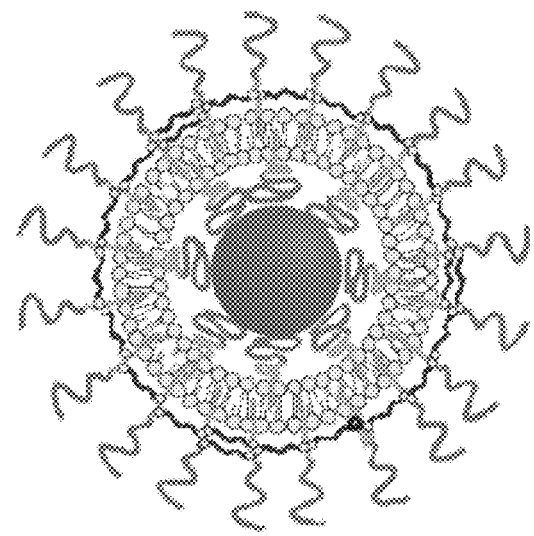
FIG. 2a is a active substance release system according to an embodiment of the invention.

FIG. 2a is an active substance release system according to an embodiment of the invention. Active substance release system 10 includes phospholipids 12. Phospholipid 12 forms a nanoparticle to carry active substance 14.

Hydrophilic or charged oligomer 16 and targeting molecule 18 is crosslinked with amphiphilic high molecular polymer 20 by hydrogen bond or electron bond to cover the surface of phospholipids 12 to protect phospholipids 12. Phospholipids 12 therefore would not contact outside proteins.

Amphiphilic high molecular polymers 20, hydrophilic or charged oligomers 16, and targeting molecules 18 are crosslinked by intermolecular hydrogen bonds or electron bonds. Amphiphilic high molecular polymers 20 have hydrophilic or charged amino acids so that amphiphilic high molecular polymers 20 are stable under a neutral condition. However, active substance 14 is released under an acidic condition because of the electrostatic repulsion of amphiphilic high molecular polymers 20.

Figure 2B:
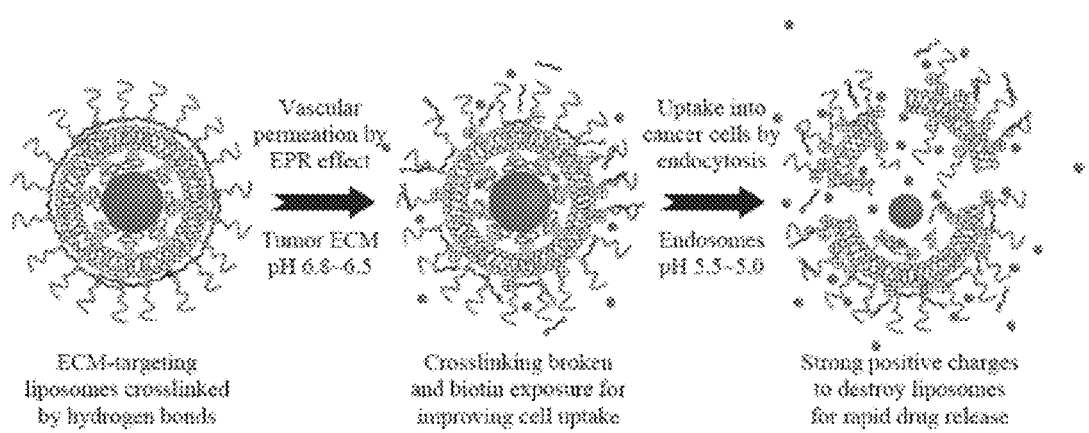
FIG. 2b is a method of delivering active substances.
Figure 3A:
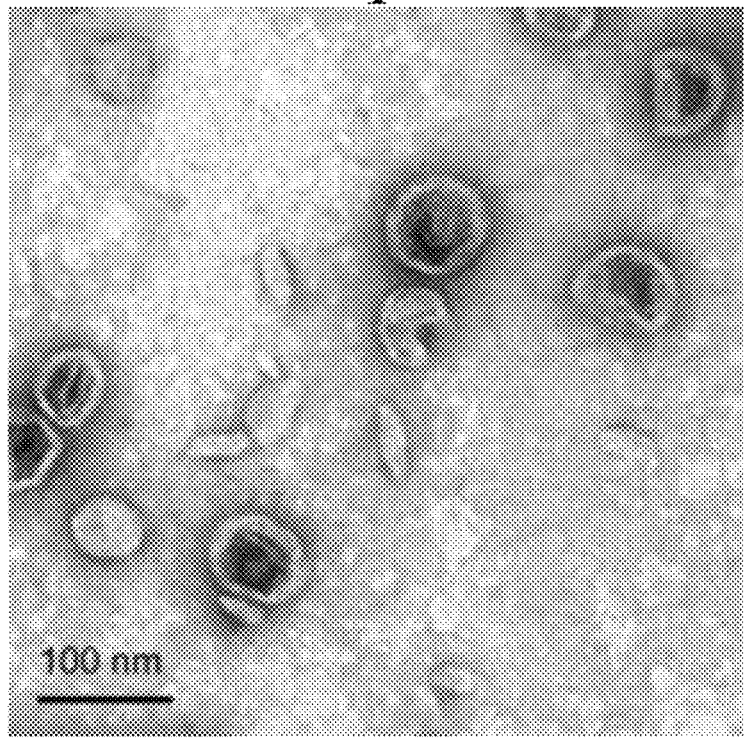
FIGS. 3a, 3b, 3c, 3d, and 3e are a microscopy images showing the nanoparticles and oligomer-contained nanoparticle complex according to the embodiments of the invention.
Figure 3B:
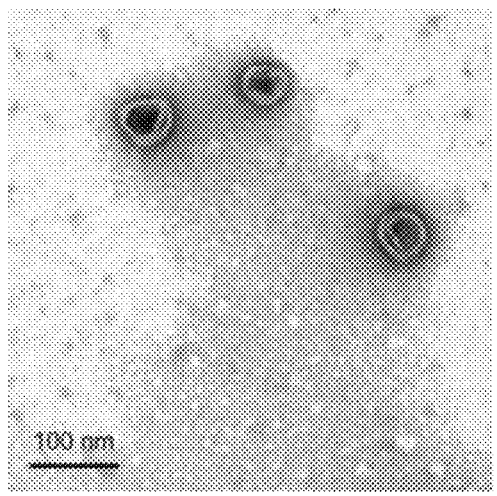
Figure 3C:
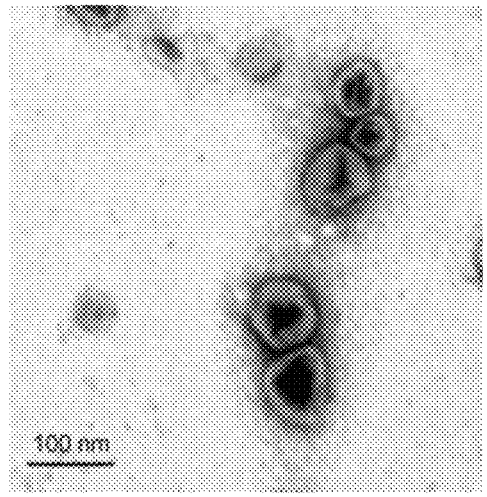
Figure 3D:
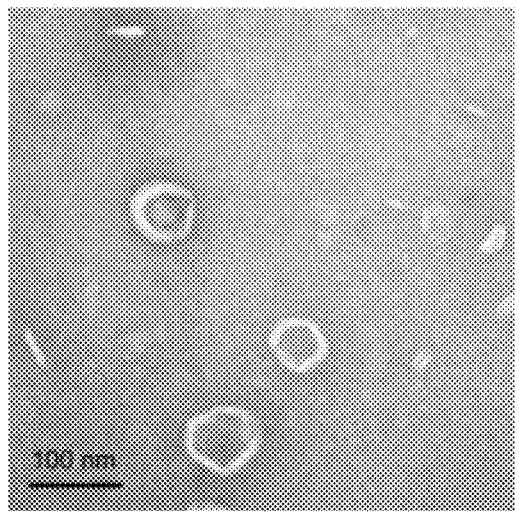
Figure 3E:
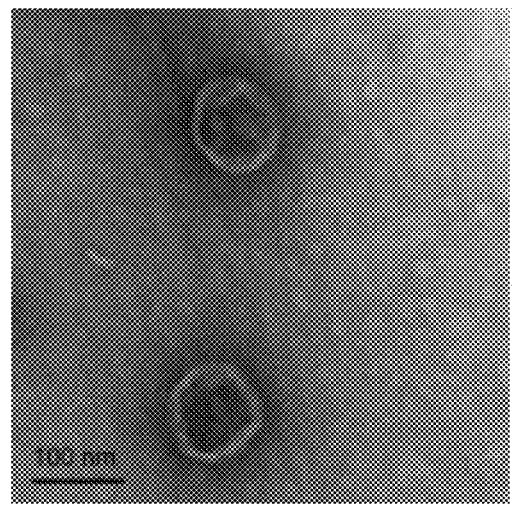

FIG. 2b shows the release active substance method of the invention. When the oligomer-contained nanoparticle complex is at weak acidic condition (extracellular matrix), the targeting molecules would be internalized into target cells (cancer cells).

When the oligomer-contained nanoparticle complex enters target cells (cancer cells), they would be dissociated by repulsive force to release the active substance (anti-cancer drugs) in target cells (cancer cells) since the polymer has hydrophilic or charged amino acids (such as His).

Accordingly, the oligomer-contained nanoparticle complex has oligomers, targeting molecules, and polymers. The oligomer and targeting molecules cover on phospholipids to protect phospholipids. Phospholipids thereof would not contact outside proteins to release active substance, and also the oligomer-contained nanoparticle complex would not be accumulated in normal tissues. Additionally, since the oligomer has hydrophilic or charged molecules, the oligomer is stable at a neutral condition, and rapidly releases the active substance at an acidic condition.

EXAMPLE

Example 1

Preparation of Nanoparticle Complex 1.1 Modification of Cholesterol

First, cholesterol (Chol, 1 mmol), succinyl anhydride (1.2 mmol), DPTS (0.3 mmol), and a small amount of triethyl amine were dissolved together in DCM. After reaction for 12 hours, the solution was extracted with an aqueous solution three times to obtain Chol-COOH. The conversion was 100% by 1H-NMR (CDCl$_3$) determination. Then, Chol-COOH (1 mmol), N-hydroxy succinimide (1.2 mmol), DPTS (0.2 mmol), and DCC (3 mmol) were dissolved in DCM. The reaction was carried out at 4° C. for 24 hours. The mixture was then extracted with an aqueous solution three times and then dried by rotary evaporation and a vacuum oven to obtain cholesterol-NHS ester.

1.2 Synthesis of Macroinitiator

The mPEG (M.W. 5000, 2 mmol), 4,4'-azobis-(4-cyanopentanoic acid) (ABCPA, 1 mmol), and 4-(dimethylamino)pyridinium-4-toluenesulfonate (DPTS, 0.3 mmol) were dissolved in DCM under $N_2$. The N,N'-Dicyclohexyl carbodiimide (DCC, 3 mmol) was also dissolved in DCM under $N_2$, and then was slowly dropped into the mPEG solution at 4° C. for reaction for 24 hours. The crude mPEG2-ABCPA was obtained by precipitating diethyl ether and drying in a vacuum oven. The dried product was further purified by ultrafiltration (membrane: Millipore, MWCO 10K) and was then freeze-dried. The polydispersity index of mPEG2-ABCPA was 1.02.

1.3 Synthesis of Polymer

First, mPEG2-ABCPA as a macroinitiator, 2-aminoethanethiol hydrochloride (AET-HCl) as a chain transfer reagent, and N-(2-hydroxypropyl) methacrylamide (HPMA) as a monomer were dissolved in ethanol under $N_2$. The reaction was conducted at 70° C. for 24 hours. The product, mPEG-PHPMA-$NH_2$, was purified by precipitation in diethyl ether. The mPEG-PHPMA-$NH_2$, was then reacted with Chol-NHS ester (1 mmol) in methanol for 24 hours to obtain mPEG-PHPMA-Chol. Final, the mPEG-PHPMA-Chol, histidine (His), DPTS, and DCC were mixed to prepare mPEG-P(HPMA-co-His)-Chol by esterification. The mole ratio of [mPEG]:[HPMA]:[His]:Chol is 1:44:14:1 or 1:47:9:1, abbreviated as "Poly_HP44His14" and "Poly_HP47His9", respectively.

1.4 Binding of Oligomer and Targeting Molecule (Biotin)

Biotin (2.4 mmol), polyethylene glycol (PEG with M.W. 200, 1 mmol), DPTS (0.2 mmol), and DCC (3 mmol) were dissolved in DMSO, and then reacted for 24 hours. After reaction, biotin2-PEG was obtained after precipitation by diethyl ether.

1.5 Preparation of Oligomer-Contained Nanoparticle Complex

The mPEG-P(HPMA-g-His)-cholesterol (1 mmole) and DPPC (34 mmole) were dissolved in DCM/methanol (1/1 v/v). A polymer-incorporated lipid thin film was formed by rotary evaporation at room temperature. Then PBS at pH 7.4 was added to rehydrate the thin film, and the solution was subjected to sonication for 6 minutes. To prepare polymer-incorporated nanoparticles, the solution was extruded by a 0.22-μm PVDF filter twice and by a 0.1-μm PVDF filter five times. To prepare oligomer-contained nanoparticle complexes, Biotin-2PEG (12.5 mmol) were added to the polymer-incorporated nanoparticles solution, shaken for 5 min, and the solution was extruded with a 0.1-μm PVDF filter twice. Characterizations of DPPC nanoparticles, polymer-incorporated nanoparticles, and oligomer-contained nanoparticle complex are shown in Table 1.

The particle size of each liposome was determined by dynamic laser scattering (DLS) (Malvern zetasizer 3000), and morphology was observed by TEM (JEM-2000 EXII) with 2% uranyl acetate staining. To determine the crosslinking level, the oligomer-contained nanoparticle complex was centrifuged by Amicon Ultra centrifugal filter (MWCO 10000). Referring to FIG. 3, the morphology of various nanoparticles was observed by transmission electron microscopy (TEM) with 2% uranyl acetate staining.

2. Stability Test

Figure 4A:
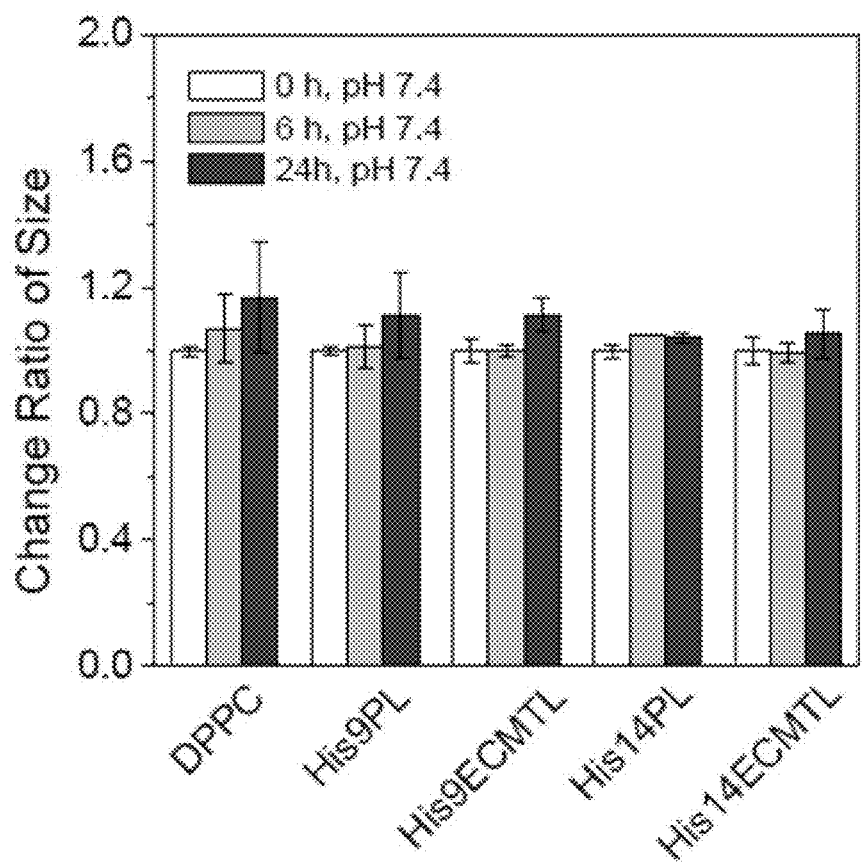
FIG. 4a shows the particle size of (a)DPPC, (b)His9PL, (c)His9ECMTL, (d)His14PL, and (e)His14ECMT at pH 7.4, respectively.
Figure 4B:
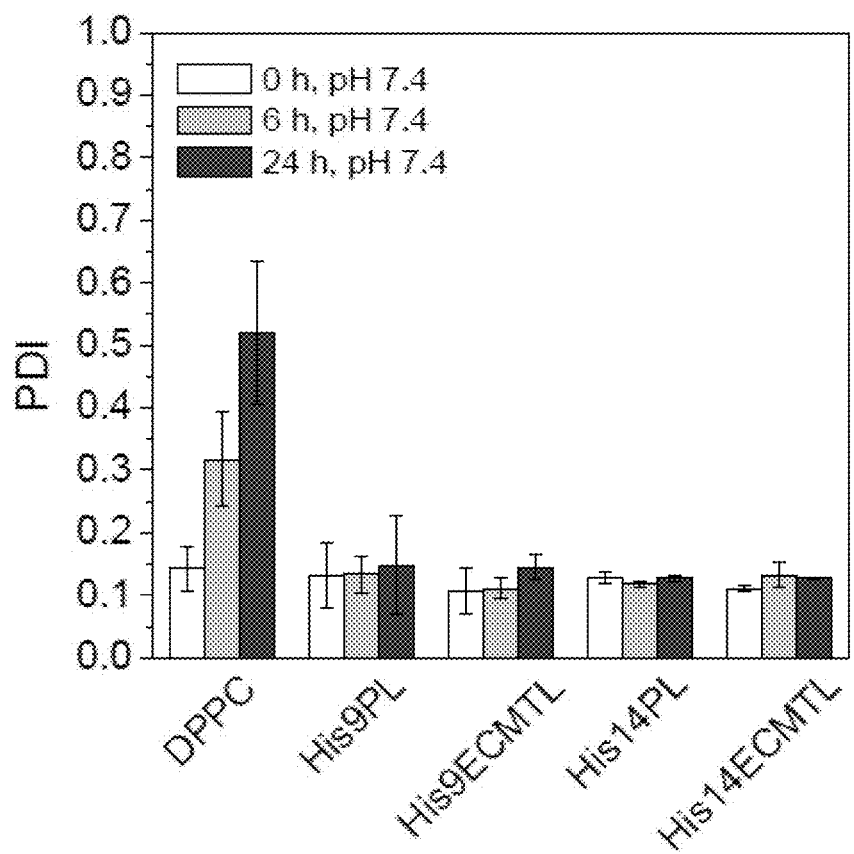
FIG. 4b shows the particle size distribution of (a)DPPC, (b)His9PL, (c)His9ECMTL, (d)His14PL, and (e)His14ECMT at pH 7.4, respectively.
Figure 4C:
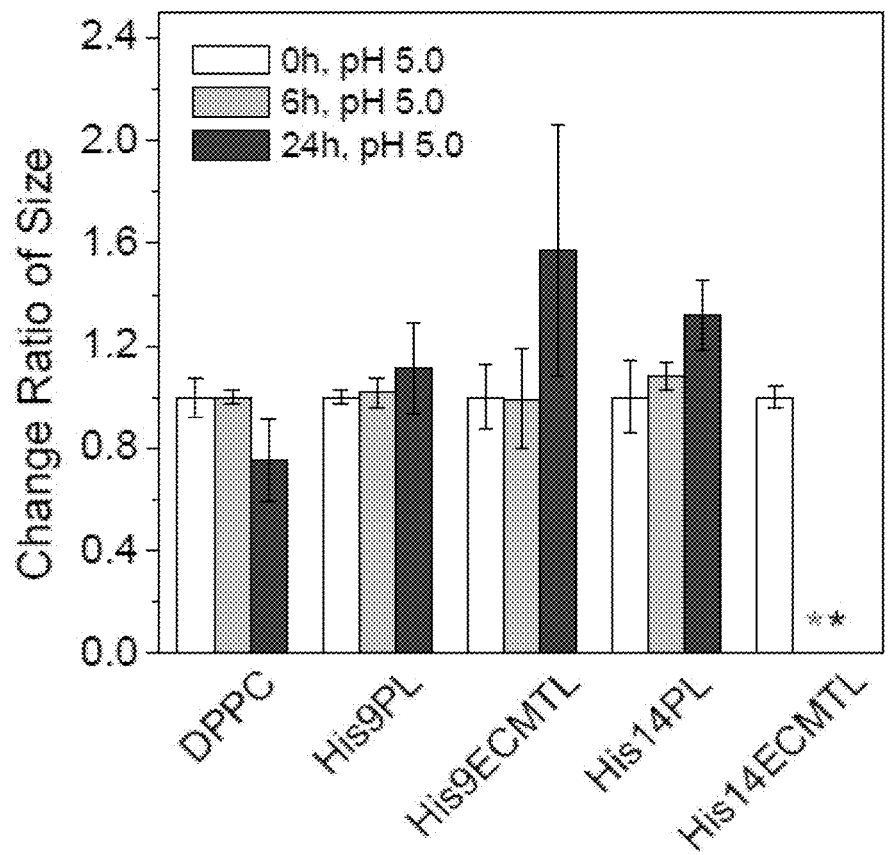
FIG. 4c shows the particle size of (a)DPPC, (b)His9PL, (c)His9ECMTL, (d)His14PL, and (e)His14ECMTL at pH 5.0, respectively.
Figure 4D:
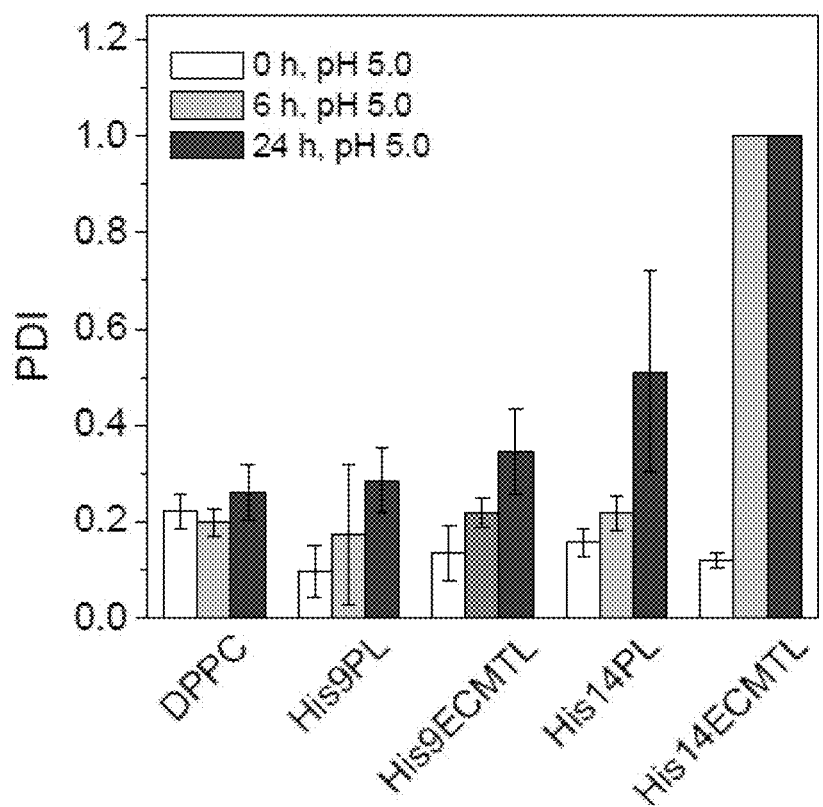
FIG. 4d shows the particle size distribution of (a)DPPC, (b)His9PL, (c)His9ECMTL, (d)His14PL, and (e)His14ECMTL at pH 5.0, respectively.
Figure 4E:
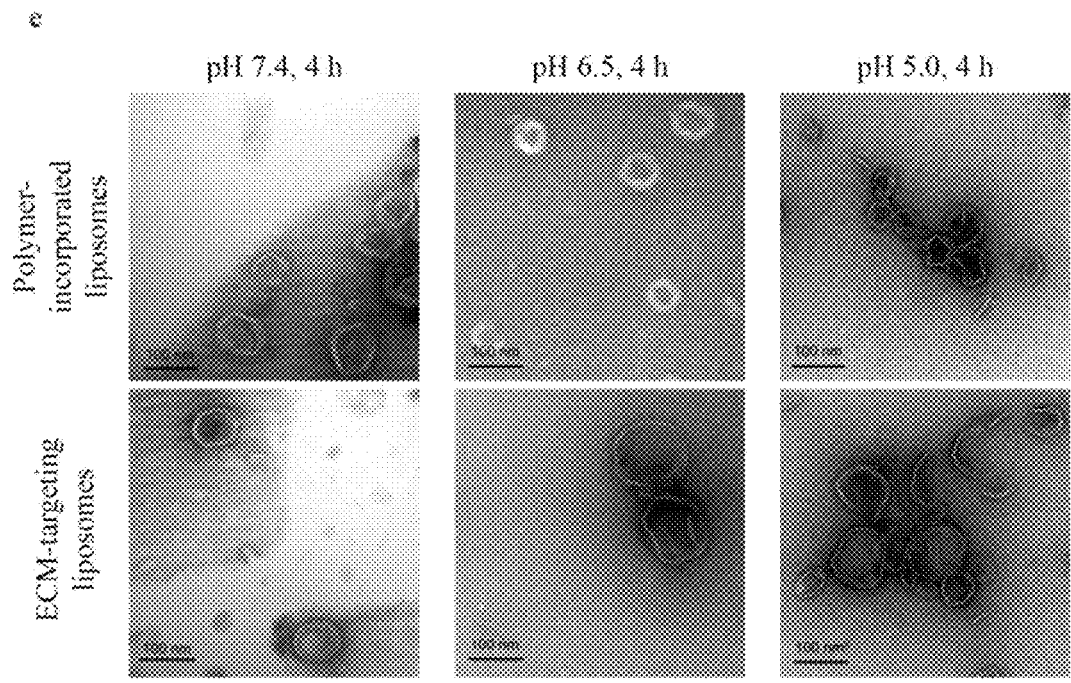
FIG. 4e is a electron microscopy image showing the nanoparticle and oligomer-contained nanoparticle complex of the invention at different pH value.
Figure 5:
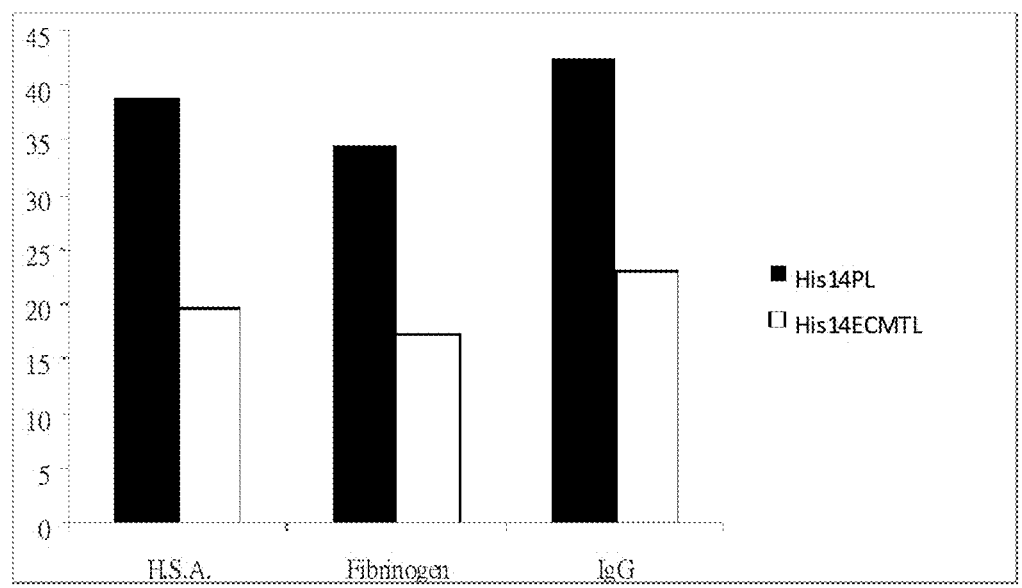
FIG. 5 shows the interaction of protein and the nanoparticle complex without oligomer.

Samples were dissolved in pH 7.4 and pH 5.0 PBS, respectively, and shaken at 200 rpm at 37° C. At various intervals, samples were analyzed by DLS. Referring to FIGS. 4a and 4b, the size and DPI of the DPPC nanoparticle increased more than those of polymer-incorporated nanoparticle and oligomer-contained nanoparticle complex, demonstrating that the DPPC nanoparticle was unstable physiologically. Referring to FIGS. 4c and 4d, the oligomer-contained nanoparticle complex with high histidine content responded rapidly to pH, unlike DPPC nanoparticle and polymer-incorporated nanoparticle with low histidine content would not rapidly to pH. The result indicates that High histidine content in nanoparticle has high pH sensitivity. FIG. 4e shows TME image of nanoparticles in the pH responsive test. The TME micrographs clearly demonstrate that the structure of oligomer-contained nanoparticle complex collapsed at pH 5.0 after treatment for 4 hours, but the structure of polymer-incorporated nanoparticle does not change.

3. Protein Interaction with Nanoparticles

Polymer-incorporated liposomes and oligomer-contained nanoparticle complex were incubated with protein PBS solutions (4 wt % albumin, 0.75 wt % fibrinogen, and 1 wt % IgG) for 24 hours at 37° C. After 24 hours incubation, the particle sizes were measured by qNano (Izon) for particle-by-paticle analysis. For qNano experiments, 40 μL of particle PBS solution with 4 wt % of HSA or with 0.1 wt % of fibrinogen was added to the fluid cell of qNano instrument and a minimum of 100 particles were recorded for each experiment. Measurements were undertaken at 50 mm of applied stretch. Referring to FIG. 4, the interaction of protein-oligomer-contained nanoparticle complex is lower than that of traditional nanoparticles.

3. Active Substance Loading

Dox in PBS (10 mg/mL) was mixed with the liposomes solution at 60° C. for 2 hours. The solution was then extruded by 0.22-μm and 0.1-μm PVDF filters. Dox-loaded polymer-incorporated liposomes were obtained after adjusting the pH of solution to 7.4. Cross-linking agents were then added into the solution to prepare Dox-loaded oligomer-contained nanoparticle complex. Excess Dox was removed by a Sephadex G-50 with the PBS mobile phase. To determine active substance content and loading efficiency, Dox-loaded polymer-

TABLE 1

Figure 6A:
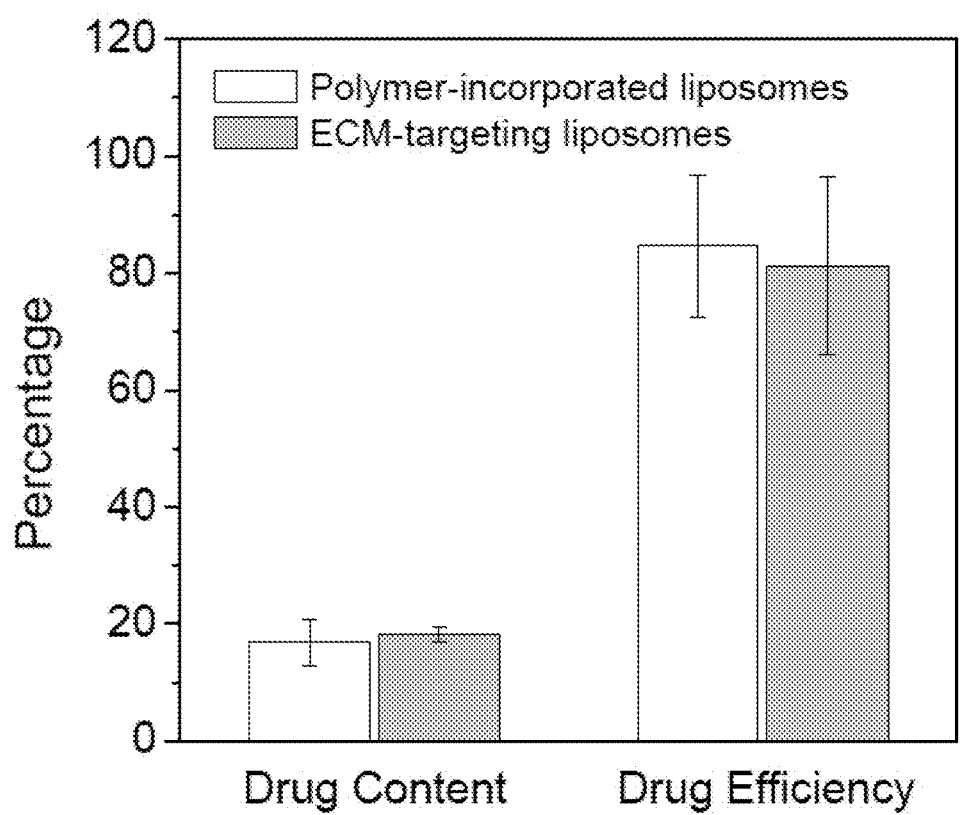
FIG. 6a shows the drug loading content and loading efficiency of the polymer-incorporated nanoparticle and oligomer-contained nanoparticle complex, respectively.
Figure 6B:
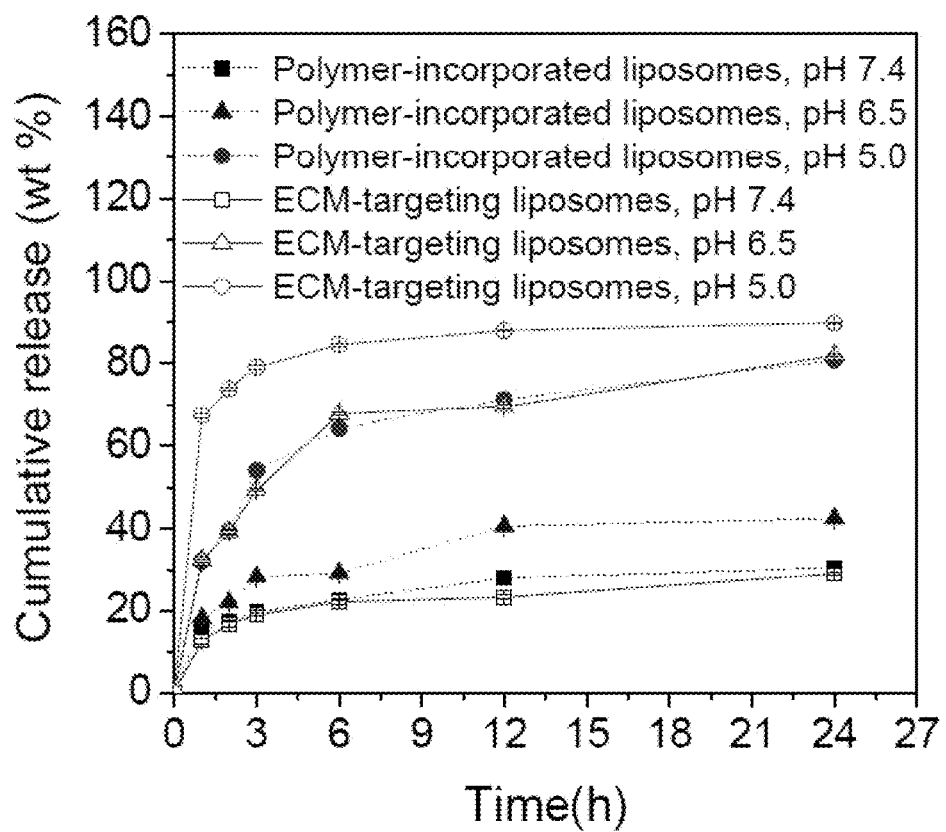
FIG. 6b shows the Dox release rate of DPPC nanoparticle, polymer-incorporated nanoparticle, and oligomer-contained nanoparticle complex at different pH value, respectively.

|  |  | Composition (wt %) | | | Particle Size | |
|---|---|---|---|---|---|---|
|  |  | Polymer | PPC | Oligomer | (nm) | DPC |
| Nanoparticle (DPPC) |  | 0 | 100 | 0 | 96.7 ± 3.7 | 0.18 ± 0.05 |
| Polymer- | His9PL | 33 | 67 | 0 | 108.4 ± 0.6 | 0.13 ± 0.02 |
| incorporated nanoparticle | His14PL | 33 | 67 | 0 | 103.9 ± 1.5 | 0.08 ± 0.02 |
| Oligomeric | His9ECMTL | 25 | 50 | 25 | 90.6 ± 1.9 | 0.14 ± 0.07 |
| nanoparticle complex | His14ECMTL | 25 | 50 | 25 | 96.2 ± 2.1 | 0.11 ± 0.03 | incorporated nanoparticles and Dox-loaded oligomer-contained nanoparticle complexes were individually dissolved in DMSO (0.5 mg/mL) for UV/Vis measurement (at 485 nm). The results show that loading efficiency of both liposomes was around 90 wt %, indicating that the outer copolymer structure did not influence active substance diffusion into the inner vesicle of liposomes and the crosslinking process did not induce active substance release, as shown in FIG. 6a.

4. Active Substance Release Assay

The release behavior of Dox from liposomes in pH 5, pH 6.5, and pH 7.4 PBS (around 0.1 mg/ml) at 37° C. was measured by HPLC with FL at 480 nm for excitation and 560 nm for emission in a time-course procedure. Dox was isolated by dialysis bag (MWCO 10000; Millipore). Chromatographic separation was performed on an Inertsil® ODS-3 column (200×4.6 mm i.d., 5 μm; GL Sciences, Japan). The mobile phase consisted of acetonitrile (A)-50 mM phosphoric acid (B) and programmed in a gradient manner as follows: A/B: 35/65 (0-10 min), 10/90 (10-15 min), and 35/65 (15-20 min). Flow rate was 1.0 ml/min. The accumulative release was calculated as: Cumulative release (%)=(Dox conc. in buffer solution)/(total Dox conc. in each sample)×100%. Referring to FIG. 6a, Both nanoparticles had a small initial burst around 20 wt % of Dox release, and then remained stable at pH 7.4. However, oligomer-contained nanoparticle complexes exhibited rapid active substance release rates for around 75 wt % and 40 wt % of Dox in the initial 2 h at pH 5.0 and 6.5, respectively. The results indicate that oligomer-contained nanoparticle complex can rapidly release active substance at a low pH value.

5. Cell Cytotoxicity

Figure 6C:
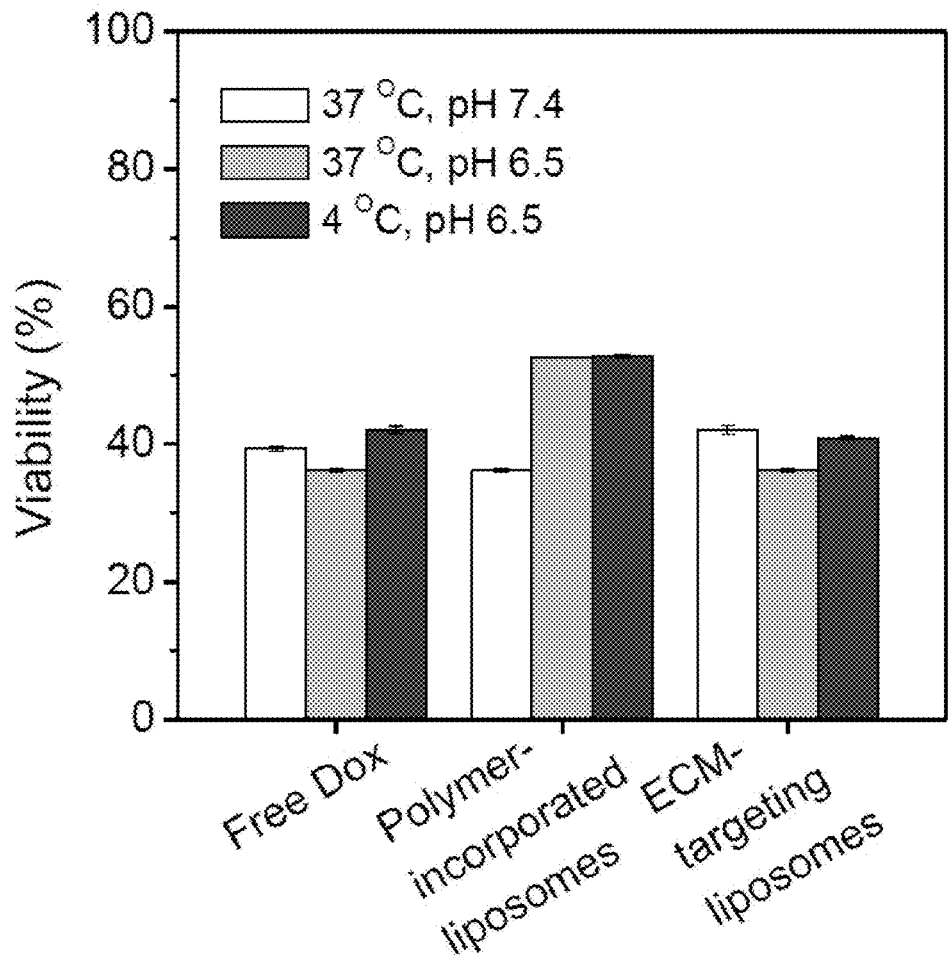
FIG. 6c shows the effect of Dox-loaded DPPC nanoparticle, polymer-incorporated nanoparticle, and oligomer-contained nanoparticle complex on cell viability, respectively.
Figure 6D:
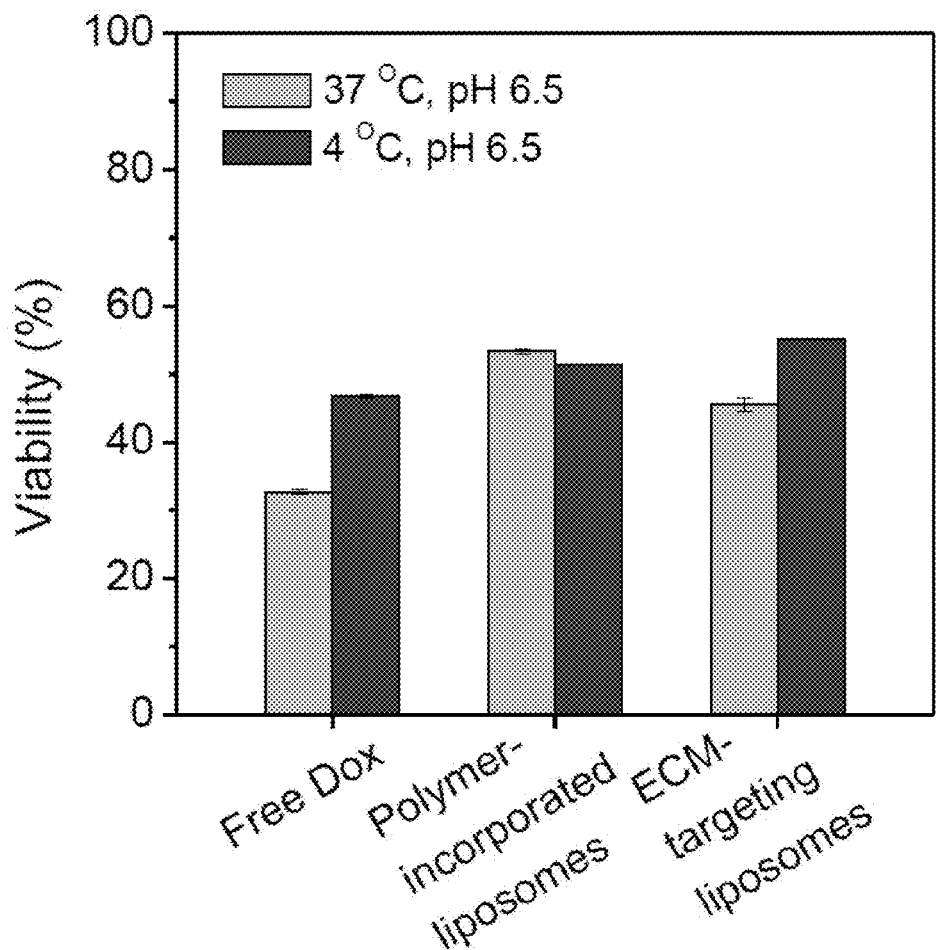
FIG. 6d shows the effect of Dox-loaded DPPC nanoparticle, polymer-incorporated nanoparticle, and oligomer-contained nanoparticle complex on HCT116 cell viability, respectively.

McCoy's 5a medium containing 10% fetal bovine serum (FBS) at pH 7.4 and pH 6.5 (adjusting using HCl) were used. First, HCT116 cells (2×104 cells/mL) were seeded on a 96-well plate and incubated in a logarithmic growth phase under 5% CO2 and 37° C. Dox-loaded oligomer-contained nanoparticle complexes, Dox-loaded polymer-incorporated nanoparticles, and free Dox medium were independently treated with HCT116 cells for 2 hours by incubation at 37° C. or 4° C. The HCT116 cells were washed twice with PBS solution, and fresh pH 7.4 medium was added for 24 hours incubation. The same procedure combined with excess of biotin molecules (75 mM) was repeated at 37° C. and 4° C. for competitive study. Referring to FIG. 6c, Dox-loaded oligomer-contained nanoparticle complexes and Dox-loaded polymer-incorporated nanoparticles had the same cell viability under pH 7.4 and 37° C. However, the cell viability of Dox-loaded oligomer-contained nanoparticle complexes was higher, significantly. The competition test with excess biotin molecules shows that the interaction between the cell membrane and active substance carriers was inhibited by excess biotin (FIG. 6d).

Figure 6E:
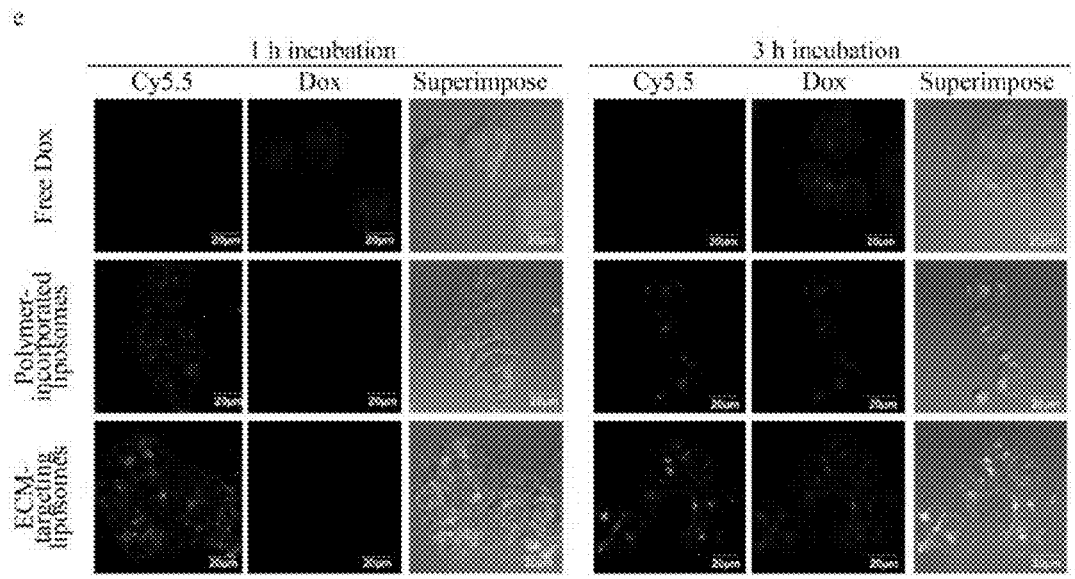
FIG. 6e shows the confocal image showing the HCT116 cells treated with Dox-loaded DPPC nanoparticle, polymer-incorporated nanoparticle, and oligomer-contained nanoparticle complex, respectively.

Accumulated liposomes and released Dox behavior in HCT116 cells were observed using a Carl Zeiss LSM5 PASCAL confocal laser scanning miscroscope (CLSM). The HCT116 cells were seeded on coverslides for 16 hours at 37° C. and then treated with Dox or liposomes for 0.5 hour at pH 6.5 and 4° C. Cells were washed twice with PBS to remove untrapped Dox or liposomes and then were cultured under pH 7.4 medium. After an interval, the cells were washed twice with PBS and mounted on a slide with 4% paraformaldehyde for CLSM observation. Fluorescence observation was carried out with a confocal microscope at 488 nm for excitation and an LP filter of 590 nm for Dox detection. Nanoparticles observation was carried out with a confocal microscope at 405 nm for excitation and an appropriate filter for FITC detection. Referring to FIG. 6e, both nanoparticle systems were internalized into cells and were located in the cytoplasm after 1 hour and Dox were released after 3 hours.

6. Biodistribution and Tumor Accumulation

Figure 7A:
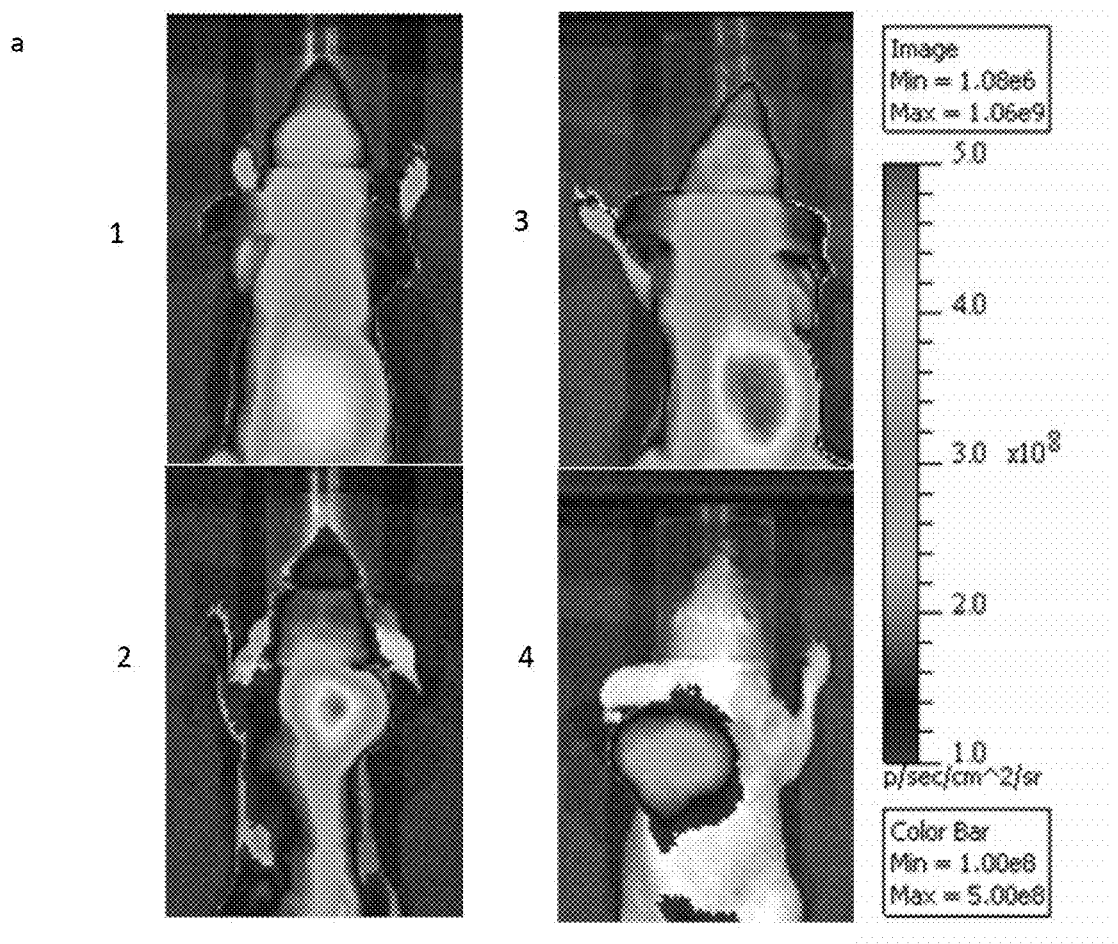
FIG. 7a shows the distribution of Dox-loaded polymer-incorporated nanoparticle and oligomer-contained nanoparticle complex in tumor mice, respectively.
Figure 7B:
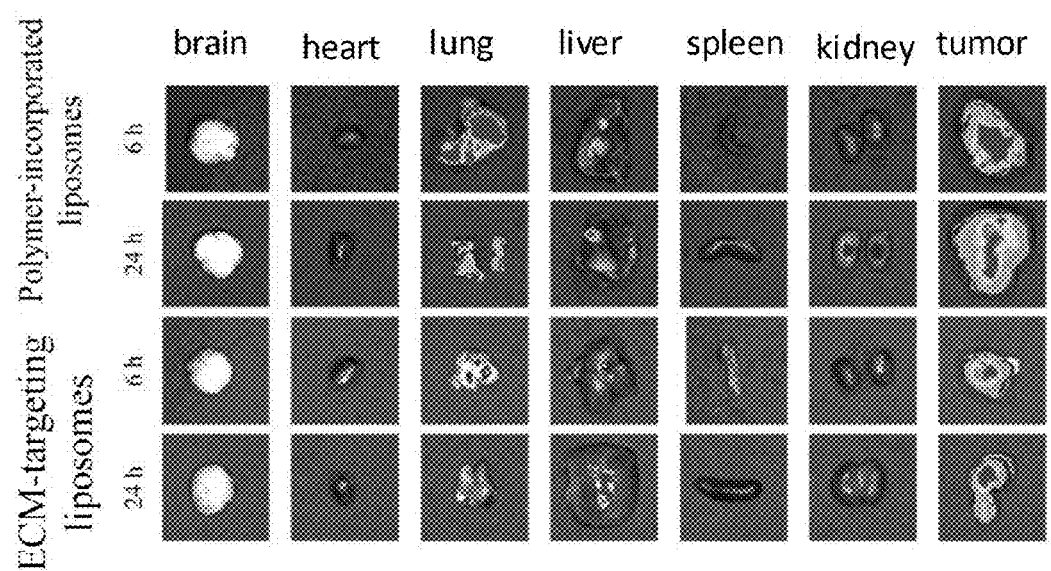
FIG. 7b shows the distribution of polymer-incorporated nanoparticle and oligomer-contained nanoparticle complex in various organs, respectively.

Fluorescent dye Cy5.5 NHS-ester was conjugated on Dox-loaded polymer-incorporated nanoparticles by NHS ester (Cy 5.5)-amine (histidine in copolymer) coupling reaction. After reaction for 2 h, Cy5.5-labeled polymer-incorporated liposomes and Cy5.5-labeled oligomer-contained nanoparticle complexes were purified by dialysis with water for 24 hours to remove excess unreacted Cy5.5. Optical imaging via the IVIS 50 imaging system was then used to evaluate the biodistribution and tumor accumulation after tail vein injection of Cy5.5-labeled polymer-incorporated nanoparticles or Cy5.5-labeled oligomer-contained nanoparticle complexes in HCT116-bearing mice. The tumor volume of tumor-bearing mice was approximately 1000 mm$^3$. The optical images for the same individual were obtained after 6 hours and 24 hours. Referring to FIG. 7a, the fluorescence of Dox-loaded oligomer-contained nanoparticle complexes in tumors was higher than that of Dox-loaded polymer-incorporated nanoparticles at 6 hours after injection. Mice were sacrificed for biodistribution observation after 6 h and 24 h. Referring to FIG. 7b, the Dox-loaded oligomer-contained nanoparticle complex was almost accumulated in tumor tissues at 24 h after injection, and a few polymer-incorporated nanoparticles were found in liver and spleen. In comparison, strong fluorescence was observed in the liver, lung, kidney, and tumor. The results indicate that oligomer-contained nanoparticle complexes can accumulated in tumor, specifically.

7. In Vivo Antitumor Activity

Figure 8A:
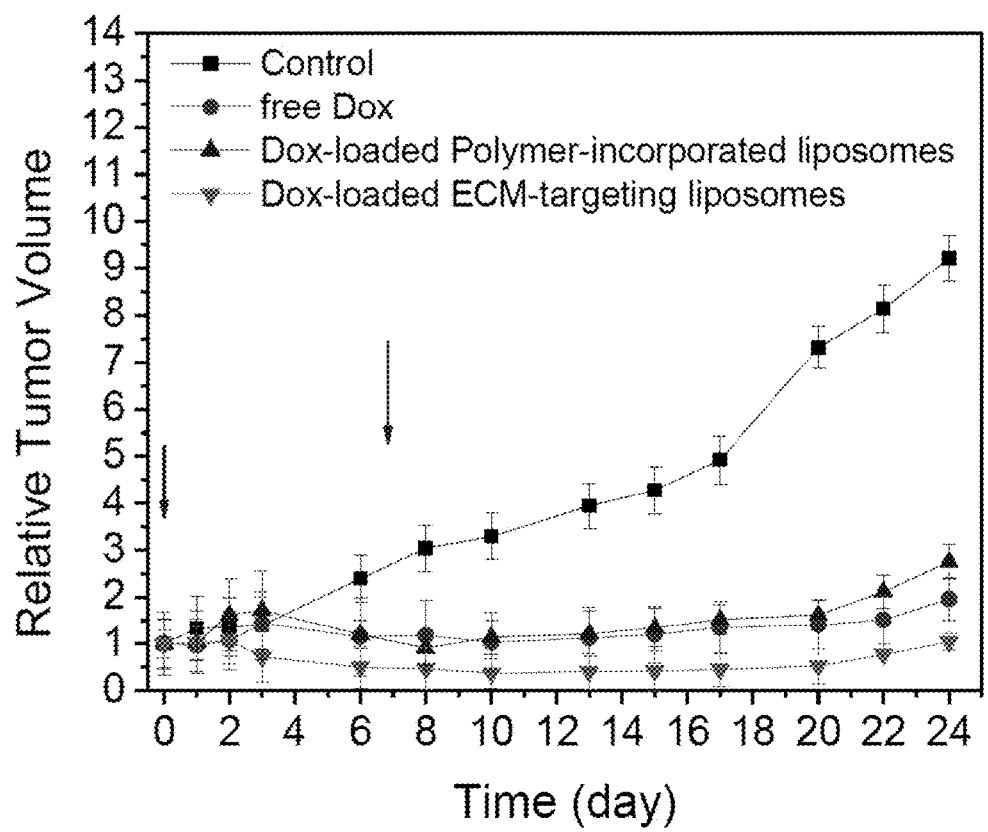
FIG. 8a shows the effect of Dox, Dox-loaded polymer-incorporated nanoparticle, and oligomer-contained nanoparticle complex on the inhibition of tumor growth.
Figure 8B:
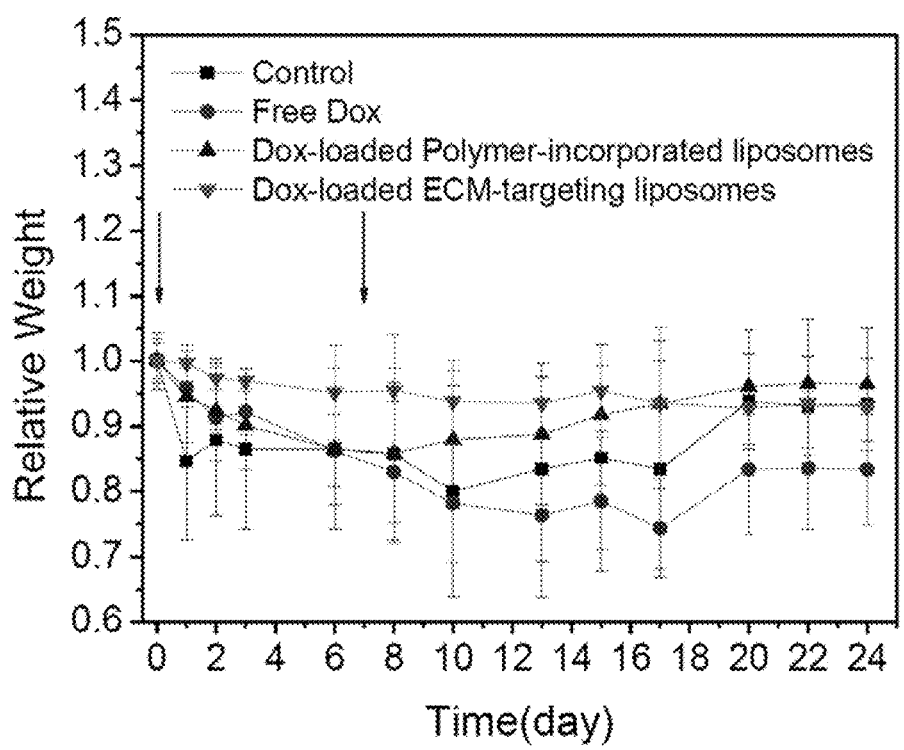
FIG. 8b shows the effect of Dox, Dox-loaded polymer-incorporated nanoparticle, and oligomer-contained nanoparticle complex on the bodyweight of mice.

The HCT116 cells were transplanted subcutaneously into the rear of 4-week female Balb-c/nude mice ($1 \times 10^6$ cells/0.1 mL) At 4-6 weeks post-transplantation, HCT116 tumor-bearing mice (tumor volume: approximately 500 mm$^3$) were used in the antitumor activity study. Mice were treated i.v. via the tail vein on days 0 and 7. Animals were then injected with a drug PBS solution (free Dox, Dox-loaded polymer-incorporated nanoparticles, and Dox-loaded oligomer-contained nanoparticle complexes at a dose of 10 mg/kg). Tumor size was measured three weekly using a Vernier's caliper. To evaluate animal wellness and clinical status, the body weight of mice was recorded. Referring to FIG. 8, compared to control mice, free Dox, Dox-loaded polymer-incorporated nanoparticles, and Dox-loaded oligomer-contained nanoparticle complexes inhibited tumor growth. Particularly, Dox-loaded oligomer-contained nanoparticle complexes had the best cancer therapy efficiency. Although free Dox and Dox-loaded polymer-incorporated nanoparticles also retarded the tumor growth rate, free Dox and Dox-loaded polymer-incorporated nanoparticles resulted in obvious weight loss during the administration period. Notably, the body weight of mice injected with Dox-loaded oligomer-contained nanoparticle complexes did not differ significantly (FIG. 8b).

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

We claim:

1. An oligomer-contained nanoparticle complex, comprising:
    a) a nanoparticle;
    b) a polymer, wherein the polymer is an amphiphilic polymer having a hydrophilic and a hydrophobic group, and the hydrophobic group is inserted on the outside of the nanoparticle;
    c) a targeting molecule, wherein an end of the targeting molecule is bonded with the hydrophilic segment of the polymer by intermolecular hydrogen bonds;

d) an oligomer, wherein the oligomer is hydrophilic or charged, and two ends of the oligomer are conjugated by covalent bonds with the targeting molecule, and e) a space for active substances, wherein the space for active substances is encapsulated by the nanoparticle.

2. The oligomer-contained nanoparticle complex as claimed in claim 1, wherein the nanoparticle is a liposome, a polymeric micelle, or a solid lipid nanoparticle.

3. The oligomer-contained nanoparticle complex as claimed in claim 1, wherein the material of the nanoparticle is selected from the group consisting of phosphatidylcholine, disteaorylphosphatidylcholine (DSPC), dimyristoylphosphatidylcholine (DMPC), dipalmitoylphosphatidylcholine (DPPC), dipalmitoylphosphatidylethanolamine (DPPE), and combinations thereof.

4. The oligomer-contained nanoparticle complex as claimed in claim 2, wherein the nanoparticle has a diameter between 0.05 μm and 0.2 μm.

5. The oligomer-contained nanoparticle complex as claimed in claim 1, wherein the hydrophobic group of the polymer is cholesterol (Chol).

6. The oligomer-contained nanoparticle complex as claimed in claim 1, wherein the hydrophilic group of the polymer comprises either a positively charged amino acid or 2-(hydroxypropyl)methacrylamide (HPMA).

7. The oligomer-contained nanoparticle complex as claimed in claim 6, wherein the positive charged amino acid is selected from the group consisting of lysine, arginine, and histidine.

8. The oligomer-contained nanoparticle complex as claimed in claim 6, wherein the oligomer is selected from the group consisting of polyethyleneglycol (PEG), polyvinylpyrrolidone (PVP), polyvinylmethylether (PVME), polymethyloxazoline (PMOX), polyethyloxazoline (PEOX), polyhydroxypropyloxazoline, polyhydroxypropylmethacrylamide (PHPMA), polymethacrylamide (PMA), polydimethylacrylamide (PDMA), polyhydroxypropylmethacrylate, polyhydroxyethylacrylate (PHEA), hydroxymethylcellulose (HMC), hydroxyethylcellulose (HEC), and polyamino acids.

9. The oligomer-contained nanoparticle complex as claimed in claim 1, wherein the targeting molecule is selected from the group consisting of folic acid, peptides, proteins, enzymes, lectins, biotin, avidin, mono-, oligo-, and polysaccharides, hormones, cytokines, and polyclonal and monoclonal antibodies.

10. The oligomer-contained nanoparticle complex as claimed in claim 1, wherein the oligomer is selected from the group consisting of polyethyleneglycol (PEG), polyvinylpyrrolidone (PVP), polyvinylmethylether (PVME), polymethyloxazoline (PMOX), polyethyloxazoline (PEOX), polyhydroxypropyloxazoline, polyhydroxypropylmethacrylamide (PHPMA), polymethacrylamide (PMA), polydimethylacrylamide (PDMA), polyhydroxypropylmethacrylate, polyhydroxyethylacrylate (PHEA), hydroxymethylcellulose (HMC), hydroxyethylcellulose (HEC), and polyamino acids.

11. The oligomer-contained nanoparticle complex as claimed in claim 1, wherein the oligomer has a molecular weight of 200-1,000 Mw.

12. The oligomer-contained nanoparticle complex as claimed in claim 1, wherein the space for active substances contains an active substance.

13. The oligomer-contained nanoparticle complex as claimed in claim 12, wherein the active substance is selected from the group consisting of a hormone, a drug, a prodrug, a toxin, a cytotoxin, a pharmaceutically active protein, an immunogen, DNA, RNA, alkylating agents, anthracycline antitumor antibiotics, antimetabolites, and metallopeptides containing one of platinum, copper, vanadium, iron, cobalt, gold, cadmium, zinc and nickel.

14. The oligomer-contained nanoparticle complex as claimed in claim 1, wherein the weight ratio of the oligomer, nanoparticle, and polymer is in a range between 0.5:2:1 and 2:2:1.

15. The oligomer-contained nanoparticle complex as claimed in claim 6, wherein the targeting molecule and the positive charged amino acid or HPMA of the hydrophilic group of the polymer are linked by intermolecular hydrogen bonds.

16. The oligomer-contained nanoparticle complex as claimed in claim 12, wherein the oligomer-contained nanoparticle complex is stable in a neutral environment having a pH value between pH 7 and pH 8.

17. The oligomer-contained nanoparticle complex as claimed in claim 12, wherein the oligomer-contained nanoparticle complex partially dissociates in a weakly acidic environment a pH value between pH 6 and pH 6.8.

18. The oligomer-contained nanoparticle complex as claimed in claim 12, wherein the active substance of the oligomer-contained nanoparticle complex is released in an acidic environment having a pH value between pH 4 and pH 6.

19. The oligomer-contained nanoparticle complex as claimed in claim 12, wherein the oligomer-contained nanoparticle complex is stable under a neutral environment having a pH between 7 and 8, partially dissociates in a weakly acidic environment having a pH between 6 and 6.8, and releases its active substance in an acidic environment having a pH between 4 and 6.

20. A method comprising:
   a) providing the oligomer-contained nanoparticle complex of claim 12;
   b) placing the oligomer-contained nanoparticle complex at a neutral environment comprising a pH between 7 and 8, wherein the oligomer-contained nanoparticle complex is stable in the neutral environment;
   c) adjusting the neutral environment to a weakly acidic environment comprising a pH of between 6 and 6.8, wherein the targeting molecule of oligomer-contained nanoparticle complex partially dissociates in the weakly acidic environment; and
   d) adjusting the weakly acidic to an acidic environment comprising a pH of between 4 and 6, wherein the active substance is released from the oligomer-contained nanoparticle complex in the acidic environment.

21. The method as claimed in claim 20, further comprising adding target cells to the weakly acidic environment.

22. The method as claimed in claim 21, wherein the target cells are selected from the group consisting of cancer cells and stem cells.

23. The method as claimed in claim 20, wherein the active substance is selected from the group consisting of a hormone, a drug, a prodrug, a toxin, a cytotoxin, a pharmaceutically active protein, an immunogen, DNA, RNA, alkylating agents, anthracycline antitumor antibiotics, antimetabolites, and metallopeptides containing one of platinum, copper, vanadium, iron, cobalt, gold, cadmium, zinc and nickel.

* * * * *